United States Patent
Koike et al.

(10) Patent No.: US 6,528,048 B1
(45) Date of Patent: Mar. 4, 2003

(54) OPHTHALMIC SOLUTIONS

(75) Inventors: Tetsuo Koike, Osaka (JP); Michiko Tsujimoto, Osaka (JP)

(73) Assignee: Rohto Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/616,726

(22) Filed: Jul. 14, 2000

Related U.S. Application Data

(63) Continuation-in-part of application No. PCT/JP99/06357, filed on Nov. 15, 1999.

(30) Foreign Application Priority Data

Nov. 16, 1998 (JP) .............................................. 10-325706

(51) Int. Cl.$^7$ ........................ A61K 31/71; A61K 31/14; A61K 25/00
(52) U.S. Cl. ............................... 424/78.17; 424/78.04; 514/912; 514/642
(58) Field of Search ............................. 424/78.17, 329, 424/78.04; 514/642, 367, 912

(56) References Cited

U.S. PATENT DOCUMENTS

| | | | |
|---|---|---|---|
| 4,407,791 A | * 10/1983 | Stark | 424/80 |
| 5,093,078 A | * 3/1992 | Hollis et al. | 424/405 |
| 5,451,398 A | * 9/1995 | Vigh | 424/78.04 |
| 5,512,597 A | * 4/1996 | Kyba et al. | 514/642 |

FOREIGN PATENT DOCUMENTS

| | | |
|---|---|---|
| WO | WO 83/01003 | 3/1983 |
| WO | WO 86/02001 | 4/1986 |
| WO | WO 90/02555 | 3/1990 |
| WO | WO 98/47359 | 10/1998 |

* cited by examiner

*Primary Examiner*—Thurman K. Page
*Assistant Examiner*—Blessing Fubara
(74) *Attorney, Agent, or Firm*—Fish & Richardson P.C.

(57) ABSTRACT

A polymer comprising quaternary ammonium salts and alkylene groups having hydroxyl groups on the main chain, is extremely useful as a disinfectant for ophthalmic apparatuses, as eye drops, and an eyewash solution as well as a cleaning solution, disinfectant, or storing solution for contact lens care. The polymer compound has sufficient bactericidal and fungicidal effects within a concentration range in which the compound causes no damage on human cells and does not irritate the eye as well as being hard to be absorbed, adsorbed, and accumulated on hydrophilic contact lenses. In addition, the compound is highly hydrophilic, and as a result, when the polymer is used for contact lens care, the lenses become favorably lubricated to be worn comfortably, and furthermore, is very gentle to eye.

23 Claims, No Drawings

OPHTHALMIC SOLUTIONS

This is a Continuation-in-part of Application No. PCT/JP99/06357, filed Nov. 15, 1999.

TECHNICAL FIELD

The present invention relates to ophthalmic solutions formulated with a polymer comprising quaternary ammonium salts and alkylene groups having hydroxyl groups on the main chain, which are highly safe for the eyes, and have a negligible adsorption onto contact lenses.

BACKGROUND ART

Anti-microbial agents often formulated as preservatives in eye drops or eyewash solutions are, for example, p-hydroxybenzoate, benzalkonium chloride, benzethonium chloride, and chlorhexidine glucuronate. However, these drugs can cause refractory corneal epithelium disorders, and accordingly there is a strong need to develop anti-microbial agents with higher levels of safety.

The development of disposable unit-dose eye drops formulated without preservatives is underway, because preservatives, when used in eye drops for the treatment of corneal disorders, may be associated with a risk of worsening the condition of the diseases. However, disposable unit-dose eye drops have several problems such as, the expense, the problem of carrying the eye drops, the waste-disposal problem of the eye drop container, etc. Thus it is desirable to develop multi-dose eye drops containing much safer preservatives.

Contact lenses are divided into two main categories, hard contact lenses and soft contact lenses. Hard contact lenses are made of polymers of acrylic esters such as poly(methyl methacrylate) and soft contact lenses are made of polymers of water-absorbing acrylic esters with hydroxyl groups such as hydroxyethyl methacrylate.

Soft contact lenses are classified into hydrophilic lenses and hydrophobic (non-hydrophilic) lenses according to the materials thereof, the hydrophilic lenses being widely popular. However, hydrophilic contact lenses not only easily absorb water but also tend to adsorb, absorb, and concentrate anti-microbial agents. Based on clinical data and basic research with animal experiments, it has been frequently pointed out that, during the use of hydrophilic contact lenses, the anti-microbial agents accumulated and concentrated in the contact lenses are released over eyes, and the release results in corneal disorders including mild disorders such as, congestion-entailing diffuse superficial keratitis, and serious disorders like corneal erosion and corneal ulcer.

Therefore, it is necessary to make various efforts when formulating eye drops that are used together with contact lenses. For example, anti-microbial agents, which are not desirable for lenses, may have to be omitted, or the formulations may have to be modified so that they are not absorbed/adsorbed onto the lenses. However, such preparations carry some defects; they are inferior in preservative effectiveness or in safety for the eyes. Preservatives formulated into the solutions for disinfecting, storing, or cleaning contact lenses also have similar problems. Although anti-microbial agents have been improved not to adversely affect the lenses, they do not satisfy both safety and preservative effectiveness.

In particular, low-molecular-weight quaternary ammonium compounds such as benzalkonium chloride and benzethonium chloride are known to have a tendency of getting absorbed/adsorbed onto contact lenses. The compounds are concentrated 400 times or more within the lenses. As compared with benzalkonium chloride, biguanides such as chlorhexidine poorly bind on the surface of contact lenses. However, it is also known that biguanides are more easily adsorbed onto lenses when protein-like materials are deposited thereon and the adsorbed compounds tend to cause ophthalmopathy such as ophthalmia.

Since these anti-microbial agents are relatively large cation molecules, they are known to interact with proteins or acidic compounds to form insoluble complexes, which cause clouding or precipitation. Therefore, these types of anti-microbial agents should not be used in ophthalmic solutions comprising acidic compounds as active ingredients or as additives. Furthermore, benzalkonium chloride affects biomembranes and causes the instability of the lacrimal oil layer. This results in the enhancement of drug permeability even at low concentrations. Because of this problem, it should be carefully used in combination with drugs. Moreover, by interacting with a surfactant, p-hydroxybenzoate forms a complex and gets trapped in the micelles, causing a reduction of the anti-microbial efficacy. Accordingly, the concentration of the surfactant used as a solubilizer should be taken into consideration. Thus, the anti-microbial agents used as preservatives in eye drops and eyewash solutions have problems to be solved in the pharmaceutical aspects as well as in safety and preservative effectiveness.

Anti-microbial agents, often formulated into disinfectants for contact lens care, are hydrogen peroxide or other microbicidal agents. In the case of hydrogen peroxide, intense congestion can be caused by the negligence of the neutralization treatment following the use of hydrogen peroxide-containing disinfectants, and therefore, can be unsafe sometimes. An example of microbicidal agents other than hydrogen peroxide is polyquad, which is a polymer of a quaternary ammonium salt and has no hydroxyl group at the cross-liking positions thereof. The uses of this polymer for disinfecting contact lenses and for preserving ophthalmic solutions have been disclosed in the Examined Published Japanese Patent Application (JP-B) No. Hei 2-54804. Another example is polyhexamethylene biguanide, and the use of the polymer for disinfecting contact lenses has been disclosed in JP-B No. Hei 6-49642. The products including these polymers are commercialized under the names of OPTI-FREE (Alcon) and ReNu (Bausch&Lomb), respectively, as new types of chemical disinfectants.

However, polyquad has an insufficient anti-microbial efficacy, while polyhexamethylene biguanide is known to be irritating to the eye. Therefore, both compounds are not satisfactory in anti-microbial efficacy or safety as microbicidal agents in ophthalmic solutions.

DISCLOSURE OF THE INVENTION

An objective of the present invention is to provide ophthalmic solutions formulated with a water-soluble compound that has an anti-microbial efficacy in a concentration range where the compound is not toxic to human cells; does not irritate the eye; is highly stable in aqueous solutions; and is hard to get absorbed, adsorbed, and accumulated on hydrophilic contact lenses.

As a result of extensive studies done by the present inventors, it was revealed that a polymer comprising quaternary ammonium salts and alkylene groups having hydroxyl groups on the main chain is highly useful for the formulation of anti-microbial agents for ophthalmic apparatuses, eye drops, eyewash solutions, as well as cleaning solutions, disinfectants, or storing solutions for contact lenses, because the polymer compound has bactericidal and fungicidal effects within a concentration range where the compound causes no damage to human cells and is not irritating to the eyes as well as being hard to get absorbed, adsorbed, and accumulated on hydrophilic contact lenses. In addition, the present inventors have found that the polymer has a structure containing many hydroxyl groups and is highly hydrophilic, and thereby, when the polymer is used for contact lens care, the lenses become favorably lubricated to be worn comfortably and furthermore, the compound itself is very gentle to eyes.

The present invention relates to ophthalmic solutions that are formulated with a polymer comprising quaternary ammonium salts and alkylene groups having hydroxyl groups on the main chain, and more specifically to:

(1) an ophthalmic solution comprising a polymer comprising quaternary ammonium salts and alkylene groups having hydroxyl groups on the main chain;
(2) the ophthalmic solution as described in (1), wherein the polymer, comprising quaternary ammonium salts and alkylene groups having hydroxyl groups on the main chain, comprises a repetitive unit represented by the following formula:

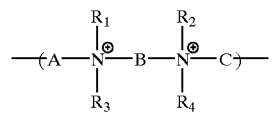

wherein R1, R2, R3, and R4 represent alkyl groups having 1 to 3 carbon atoms; A, B, and C represent alkylene groups having 1 to 3 carbon atoms, oxyalkylene groups having one to three carbon atoms, or alkylene groups having 1 to 4 carbon atoms and one or more hydroxyl groups; and at least one of the alkylene groups, A, B, and C, has one or more hydroxyl groups, and counter ion(s);
(3) the ophthalmic solution as described in (2), wherein the repetitive unit is represented by the following formula:

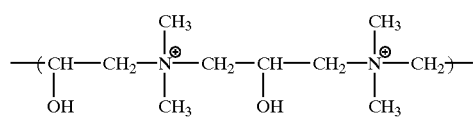

or the following formula:

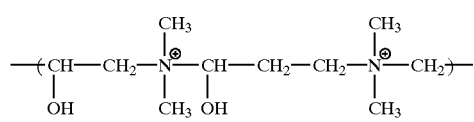

(4) the ophthalmic solution as described in any one of (1) to (3), wherein the counter ion is chloride ion(s);
(5) the ophthalmic solution as described in any one of (1) to (4), wherein said polymer comprising quaternary ammonium salts and alkylene groups having hydroxyl groups on the main chain, is contained at a concentration ranging from 0.00001 to 1.0 w/v %;
(6) the ophthalmic solution as described in (5), which is a disinfectant for ophthalmic apparatuses;
(7) the ophthalmic solution as described in any one of (1) to (4), wherein said polymer comprising quaternary ammonium salts and alkylene groups having hydroxyl groups on the main chain, is contained at a concentration ranging from 0.00001 to 0.01 w/v %;
(8) the ophthalmic solution as described in (7), which is an eye drop, an eyewash solution, or a cleaning solution, a storing solution, a disinfectant, a cleaning-storing solution, or a cleaning-disinfecting-storing solution used for the care of contact lenses;
(9) the ophthalmic solution as described in (8), wherein the polymer, which comprises quaternary ammonium salts and alkylene groups having hydroxyl groups on the main chain, has an adequate molecular weight ensuring that the polymer is not substantially adsorbed onto and/or absorbed into hydrophilic contact lenses;
(10) the ophthalmic solution as described in (9), wherein the polymer, which comprises quaternary ammonium salts and alkylene groups having hydroxyl groups on the main chain, has a molecular weight ranging from 1000 to 100000;
(11) the ophthalmic solution as described in any one of (1) to (10), further comprising aspartic acid and/or a salt thereof; and
(12) the ophthalmic solution as described in (11), wherein the salt is selected from the group consisting of sodium aspartate, potassium aspartate, and magnesium aspartate.

The "ophthalmic solution" referred to in the present invention indicates a solution that is directly applied to or contacts with ophthalmic tissues, as well as a solution for treating contact lenses or ophthalmic apparatuses. The solution includes, for example, eye drops, eyewash solutions, and solutions for contact lens care and disinfectants for ophthalmic apparatuses. The solutions for contact lens care as referred herein include single- or multi-functional solutions for the care of contact lenses used as a disinfecting solution, a cleaning solution, a storing solution, a cleaning-storing solution, a cleaning-disinfecting-storing solution, or the like.

The ophthalmic solution of the present invention is characterized by comprising a polymer comprising quaternary ammonium salts and alkylene groups having hydroxyl groups on the main chain. The preferable polymer, contained in the ophthalmic solutions of the present invention, is exemplified by a compound comprising a repetitive unit having counter ion(s). The repetitive unit is represented by the following formula:

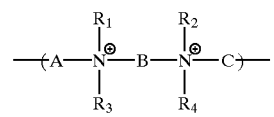

wherein R1, R2, R3, and R4 represent alkyl groups having 1 to 3 carbon atoms; A, B, and C represent alkylene groups having 1 to 3 carbon atoms, oxyalkylene groups having 1 to 3 carbon atoms, or alkylene groups having 1 to 4 carbon atoms and one or more hydroxyl groups; and at least one of the alkylene groups, A, B, and C, has one or more hydroxyl groups.

In the above formula, the groups represented by R1, R2, R3, and R4 are, for example, —$CH_3$, —$C_2H_5$, and —$C_3H_7$. The groups represented by A and C, are exemplified by —$CH_2$—, —$C_2H_4$—, —$OC_2H_4$—, —$OC_3H_6$—, —CH(OH)—, —CH(OH)—$CH_2$—, and —$CH_2$—CH(OH)—. The group represented by B includes, for example, —$CH_2$—, —$C_2H_4$—, —$OC_2H_4$—, —$OC_3H_6$—, —CH(OH)—, —CH(OH)—$CH_2$—, —$CH_2$—CH(OH)—, —CH(OH)—$CH_2$—$CH_2$—, —$CH_2$—CH(OH)—$CH_2$—, —$CH_2$—$CH_2$—CH(OH)—, —CH(OH)—$CH_2$—$CH_2$—

CH$_2$—, —CH(OH)—CH$_2$—CH$_2$—, —CH$_2$—CH$_2$—CH(OH)—CH$_2$—, and —CH$_2$—CH$_2$—CH$_2$—CH(OH)—. The counter ion includes, for example, F$^-$, Cl$^-$, Br$^-$, I$^-$, SO$_4^{2-}$, HSO$_3^-$, H$_2$PO$_4^-$, HPO$_4^{2-}$, PO$_4^{3-}$, HCO$_3^-$, CO$_3^{2-}$, and R—CO$_2^-$ (R is an alkyl group or an alkylene group); the counter ion(s) form a salt together with the polymer by interacting with the positive charges on the polymer. The compound may be a chain polymer or linear polymer; however, there is no special limitation to the form of the polymer, as long as the anti-microbial efficacy is not affected by the form thereof.

Among the compounds represented by the formula as shown above, the preferred is, for example, a compound composed of a repetitive unit represented by the following formula (designated as compound (1)):

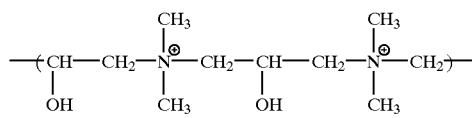

or a compound composed of a repetitive unit represented by the following formula (designated as compound (2)):

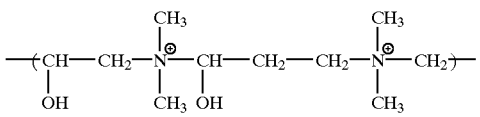

These preferable compounds have hydroxyl groups that are contained in the hydroxypropylene groups, as seen in the formulae. A commercial product (a disinfectant for swimming pool), named GLOKILL PQ manufactured by Rhodia, contains a 50% concentration of the chloride salt of compound (1) (designated as compound (3) herein), having an average molecular weight of about 10000.

It is generally believed that the microbicidal efficacy of a high-molecular-weight compound is inversely proportional to the molecular weight thereof. However, the compound (3) included in GLOKILL PQ possesses a sufficient microbicidal efficacy and is larger in size than the pore size of the polymer matrix of contact lenses, and as a consequence, compound (3) is poorly absorbed/adsorbed onto contact lenses (Test example 4). Compound (3) also has a broad anti-microbial spectrum and exhibited biocidal activity against gram-positive and gram-negative bacteria, and fungi at an extremely low concentration (Test examples 1 and 2). It did not cause any conjunctival or corneal damage to the ophthalmic mucous membrane in the irritation test using rabbit eyes (Test example 5). Thus it can be concluded that the compound is highly safe for the eyes.

Compound (2) contains hydroxypropylene groups having hydroxyl groups at the α' positions and therefore, there are many hydroxyl groups in the molecule. Based on the structural similarity to compound (3), compound (2) is assumed to have the same activity.

Thus the compound contained in the ophthalmic solutions of the present invention, is a polymer containing quaternary ammonium salts and alkylene groups having hydroxyl groups, and therefore, is characterized by the large amount of hydroxyl groups and quaternary ammonium groups as well as possessing an equivalent activity to that of compound (3).

The ophthalmic solutions of the present invention are formulated with the compound usually at a concentration ranging from 0.00001 to 1.0 w/v %, preferably from 0.00001 to 0.1 w/v %. For example, disinfectants for ophthalmic apparatuses are formulated using the compound usually at a concentration ranging from 0.00001 to 1.0 w/v %, preferably from 0.00001 to 0.1 w/v %. Eyedrops, eyewash solutions, or cleaning solutions, storing solutions, or cleaning-storing solutions used for contact lens care are formulated using the compound usually at a concentration ranging from 0.00001 to 0.01 w/v %, preferably from 0.00005 to 0.005 w/v %. Disinfectants and cleaning-disinfecting-storing solutions used for contact lens care are formulated using the compound usually at a concentration ranging from 0.00001 to 0.01 w/v %, preferably from 0.00001 to 0.001 w/v %.

In the ophthalmic solutions of the present invention, the preferable average molecular weight of the compound ranges from 500 to 100000. When the above-mentioned compound is used to formulate solutions for contact lens care and the eye drops used together with contact lenses, preferably, the compound has an adequate molecular weight to ensure that it is not substantially adsorbed onto and/or absorbed into hydrophilic contact lenses. In this case, the preferable average molecular weight of the compound ranges from 1000 to 100000. The number of the repetitive units is preferably 2 to 500, more preferably 5 to 500.

There is no restriction on the pH of the ophthalmic solutions of the present invention as long as the pH is within the ophthalmologically acceptable range; the pH value usually ranges from about 5.0 to 9.0, preferably from 5.5 to 8.5. The osmotic pressure ratio (the ratio of osmotic pressure of the ophthalmic solution to the osmotic pressure of physiological saline) is usually adjusted to about 0.5 to 5.0, preferably adjusted to about 0.8 to 2.0.

The ophthalmic solutions of the present invention can be formulated with various ingredients besides the compound. There are no restrictions on the ingredients contained in the solutions. For example, the solutions may be formulated with a variety of additives such as buffering agents, isotonizing agents, solubilizers, stabilizers, viscoelastic agents, chelating agents, and pH-adjusting agents as well as active ingredients such as agents for removing congestion, anti-inflammatory agents, astringents, antihistaminic agents, anti-microbial agents, vitamins, amino acids, inorganic salts, and saccharides. For example, the solutions may also contain coloring agents such as 1-menthol.

The buffering agents include, for example, borate buffer, phosphate buffer, carbonate buffer, acetate buffer, citrate buffer, e-aminocapronic acid, glutamic acid and salts thereof, and aspartic acid and salts thereof.

The isotonizing agents include, for example, sodium chloride, potassium chloride, calciumchloride, glycerol, glucose, mannitol, aminoethyl sulfonic acid, aspartic acid, potassium aspartate, sodium aspartate, and magnesium potassium aspartate. In particular, the preferable isotonizing agents are aspartic acid and/or salts thereof; the salts preferred are sodium aspartate, potassium aspartate, and magnesium aspartate. The ophthalmic solutions are formulated with a solution of aspartic acid and/or salts thereof that is isotonic with 0.5 to 2.0% sodium chloride solution. The ophthalmic solutions containing aspartic acid and/or its salts at a concentration adjusted within a range where they exert no adverse influences on the properties of soft contact lenses, for example, such as the shape thereof, are preferably used as solutions for contact lens care, because these have no negative influences on the anti-microbial activity of the compound. Furthermore, aspartic acid is also useful as a buffering agent because of the buffering action thereof.

The solubilizers include, for example, polyoxyethylene hydrogenated castor oil, polyethylene glycol, propylene glycol, polysorbate 80, polyoxyethylene-polyoxypropylene glycol, urea, and ethanol.

The stabilizers include, for example, sodium hydrogen sulfite, sodium sulfite, sodium thiosulfate, sodium pyrosulfite, sodium metabisulfite, and sodium edetate.

The viscoelastic agents include, for example, methyl cellulose, carboxymethyl cellulose, hydroxyethyl cellulose, hydroxypropylmethyl cellulose, polyvinyl alcohol, polyvinyl pyrrolidone, dextran, chondroitin sulfate and salts thereof, and hyaluronic acid and salts thereof.

The chelating agents include, for example, sodium edetate, and citric acid and salts thereof. The pH-adjusting agents include, for example, sodium hydroxide, potassium hydroxide, sodium carbonate, hydrochloric acid, acetic acid, citric acid, and phosphoric acid.

To improve the detergency, the solutions for cleaning, disinfecting, and/or storing contact lenses can be formulated with, for example, nonionic surfactants, amphoteric surfactants, or anionic surfactants.

The nonionic surfactants include, for example, polyoxyethylene-polyoxypropylene glycol, sorbitan fatty acid ester, glycerol fatty acid ester, poly(glycerol fatty acid ester), polyoxyethylene sorbitan fatty acid ester, polyoxyethylene sorbitol fatty acid ester, polyoxyethylene glycerol fatty acid ester, polyethylene glycol, polyoxyethylene alkyl ether, polyoxyethylene alkyl phenyl ether, polyoxyethylene hydrogenated castor oil, polyoxyethylene alkylamine, and polyoxyethylene fatty acid amide.

The amphoteric surfactants include, for example, alkyl dimethylaminoacetic acid betaine, fatty acid amide propyldimethylaminoacetic acid betaine, and polyalkylaminoethyl glycine.

The anionic surfactants include, for example, alkyl sulfate, polyoxyethylene alkyl ether sulfate, N-acyl amino acid salt, polyoxyethylene alkyl ether acetate, alkyl sulfocarboxylate, α-olefin sulfonate, and polyoxyethylene alkyl ether phosphate. The ophthalmic solutions of the present invention thus prepared are stable aqueous liquid preparations and can be used for a long period of time at normal temperatures. Even when used at a low concentration, the polymer compound has a high preservative efficacy in the solutions. In addition, the compound is highly safe, since it exhibits only negligible toxicity to corneal epithelial cells. Furthermore, the compound is not adsorbed onto hydrophilic contact lenses, although hydrophilic lenses are highly absorptive and adsorptive for drugs in nature. Thus, the ophthalmic solutions of the present invention are applicable to all types of soft contact lenses and hard contact lenses.

BEST MODE FOR CARRYING OUT THE INVENTION

Preferred embodiments of the present invention will be illustrated below with reference to Examples, but these examples are not to be construed to limit the scope of the present invention.

EXAMPLE 1
Artificial Tear-type Eye Drops

| | |
|---|---|
| Compound (3) | 0.0005 g |
| Sodium chloride | 0.700 g |
| Potassium chloride | 0.100 g |
| Boric acid | 1.000 g |
| Borax | 0.200 g |
| Sodium edetate | 0.050 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Boric acid and borax are added and dissolved in the sodium edetate solution. Sodium chloride and potassium chloride, and subsequently, compound (3), are added and dissolved in the solution. The pH is adjusted to about 7.4 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 2
Artificial Tear-type Eye Drops

| | |
|---|---|
| Compound (3) | 0.0001 g |
| Sodium chloride | 0.500 g |
| Potassium chloride | 0.080 g |
| Sodium dihydrogen phosphate | 0.150 g |
| Disodium hydrogen phosphate | 0.100 g |
| Sodium edetate | 0.005 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Sodium dihydrogenphosphate and disodium hydrogenphosphate are added and dissolved in the sodium edetate solution. Sodium chloride and potassium chloride, and subsequently, compound (3), are added and dissolved in the solution. The pH is adjusted to about 7.4 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 3
Eye Drops for Removing Congestion

| | |
|---|---|
| Compound (3) | 0.0005 g |
| Naphazoline hydrochloride | 0.003 g |
| Boric acid | 1.000 g |
| Borax | 0.030 g |
| Sodium edetate | 0.050 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Boric acid and borax are added and dissolved in the sodium edetate solution. Naphazoline hydrochloride, and subsequently, compound (3), are added and dissolved in the solution. The pH is adjusted to about 7.4 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 4

Anti-inflammatory Eye Drops

| | |
|---|---|
| Compound (3) | 0.0005 g |
| Dipotassium glycyrrhizinate | 0.250 g |
| Chlorpheniramine maleate | 0.030 g |
| Boric acid | 1.000 g |
| Borax | 0.030 g |
| Sodium edetate | 0.050 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Boric acid and borax are added and dissolved in the sodium edetate solution. Dipotassium glycyrrhizinate and Chlorpheniramine maleate, and subsequently, compound (3), are added and dissolved in the solution. The pH is adjusted to about 6.0 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 5

Disinfectant for Contact Lens

| | |
|---|---|
| Compound (3) | 0.0005 g |
| Sodium chloride | 0.900 g |
| Boric acid | 1.000 g |
| Borax | 0.200 g |
| Sodium edetate | 0.050 g |
| Hydroxyethyl cellulose | 0.100 g |
| Poloxamer 407 | 0.100 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Boric acid and borax are added and dissolved in the sodium edetate solution. Sodium chloride, and subsequently, compound (3), are added and dissolved in the solution. The pH is adjusted to about 7.4 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 6

Cleaning-disinfecting-storing Solution for Contact Lenses

| | |
|---|---|
| Compound (3) | 0.00005 g |
| Sodium chloride | 0.900 g |
| Boric acid | 1.000 g |
| Borax | 0.200 g |
| Sodium edetate | 0.050 g |
| Polyvinylpyrrolidone K-90 | 2.000 g |
| Poloxamer 407 | 0.100 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Boric acid and borax are added and dissolved in the sodium edetate solution. Sodium chloride, and subsequently, compound (3), Polyvinylpyrrolidone K-90 and Poloxamer 407, are added and dissolved in the solution. The pH is adjusted to about 7.4 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 7

Eyewash Solution

| | |
|---|---|
| Compound (3) | 0.0001 g |
| Dipotassium glycyrrhizinate | 0.025 g |
| Boric acid | 1.550 g |
| Borax | 0.300 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, boric acid and borax are dissolved little by little in about 80 ml of purified water. Dipotassium glycyrrhizinate, and subsequently, compound (3) are added and dissolved in the solution. The pH is adjusted to about 7.4 by using 0.1N sodium hydroxide solution and 0.1N hydrochloric acid. The total volume of the solution is adjusted to 100 ml. The solution is then filtrated through a 0.2 μm-cellulose acetate filter. Finally, a sterilized plastic container is filled with the solution.

EXAMPLE 8

Cleaning-disinfecting-storing Solution for Contact Lenses

| | |
|---|---|
| Compound (3) | 0.001 g |
| Potassium aspartate | 2.000 g |
| Disodium hydrogenphosphate | 0.100 g |
| Sodium edetate | 0.050 g |
| Hydroxypropylmethyl cellulose | 0.050 g |
| Poloxamer 407 | 0.100 g |
| 0.1N sodium hydroxide solution | Adequate amount |
| 0.1N hydrochloric acid | Adequate amount |
| Sterile purified water | Adequate amount |
| Total amount | 100 ml |

In the first step of preparing the solution, sodium edetate is dissolved little by little in about 80 ml of purified water. Disodium hydrogenphosphate is added and dissolved. Potassium aspartate, and subsequently, compound (3), hydroxypropylmethyl cellulose, and poloxamer 407 are added and dissolved in the solution. The pH is adjusted to about 7.4 by using 0.1N sodium hydroxide solution and 0.1N hydrochloric acid. The total volume of the solution was adjusted to 100 ml. The solution is then filtrated through a 0.2 μm-cellulose acetate filter. Finally, a sterilized plastic container is filled with the solution.

Test Example 1
Preservative Effect of Compound (3)

Test solutions as formulated in Table 1 (g/100 ml) were prepared as eye drops containing compound (3) as a preservative. A test solution formulated with a mixture of methylparaben and propylparaben, and a test solution formulated with potassium sorbate were also prepared for the control test.

Preservative efficacy test was conducted for the test solutions and the control solutions according to the USP preservative effectiveness test by using *Staphylococcus aureus, Pseudomonas aeruginosa, Escherichia coli, Serratia marcescens, Candida albicans,* and *Aspergillus niger.* The viable count of the microorganisms was determined 2 days and 7 days after the initiation of the test to evaluate the preservative effect.

The results are shown in Table 2 and Table 3. It is clear that the compound of the present invention has a sufficient preservative efficacy at a very low concentration. In contrast, the preservative condition of the aqueous liquid preparation is not satisfactorily maintained by using other preservatives such as parabens and potassium sorbate even at high concentrations.

TABLE 1

|  | Formulations | | | | | |
| --- | --- | --- | --- | --- | --- | --- |
|  | 0 | 1 | 2 | 3 | 4 | 5 |
| Compound (3) | 0.0100 | 0.0100 | 0.0010 | 0.0002 | | |
| Potassium sorbate | | | | | | 0.1000 |
| Methylparaben | | | | | 0.1000 | |
| Propylparaben | | | | | 0.0200 | |
| Boric acid | | 1.0000 | 1.0000 | 1.0000 | 1.0000 | 1.0000 |
| Borax | | 0.2000 | 0.2000 | 0.2000 | 0.2000 | 0.2000 |
| Sodium edetate | | 0.0500 | 0.0500 | 0.0500 | 0.0500 | 0.0500 |
| Sodium hydroxide | Adequate amount | Adequate amount | Adequate amount | Adequate amount | Adequate amount | Adequate amount |
| Sterile purified water | Adequate amount | Adequate amount | Adequate amount | Adequate amount | Adequate amount | Adequate amount |
| pH | 7.4 | 7.4 | 7.4 | 7.4 | 7.4 | 7.4 |

TABLE 2

Viability (%); 2 days after the initiation of the test

|  | Formulations | | | | | |
| --- | --- | --- | --- | --- | --- | --- |
| Strains | 0 | 1 | 2 | 3 | 4 | 5 |
| *Staphylococcus aureus* | <0.01 | <0.01 | <0.01 | <0.01 | 100 | 0.13 |
| *Pseudomonas aeruginosa* | <0.01 | <0.01 | <0.01 | <0.01 | 6.2 | <0.01 |
| *Escherichia coli* | <0.01 | <0.01 | <0.01 | <0.01 | 7.2 | <0.01 |
| *Serratia marcescens* | <0.01 | <0.01 | <0.01 | <0.01 | 9.4 | <0.01 |
| *Candida albicans* | <0.01 | <0.01 | <0.01 | <0.01 | 37 | 11 |
| *Aspergillus niger* | <0.01 | <0.01 | <0.01 | <0.01 | 71 | 5.3 |

TABLE 3

Viability (%); 7 days after the initiation of the test

|  | Formulations | | | | | |
| --- | --- | --- | --- | --- | --- | --- |
| Strains | 0 | 1 | 2 | 3 | 4 | 5 |
| *Staphylococcus aureus* | <0.01 | <0.01 | <0.01 | <0.01 | 7.5 | <0.01 |
| *Pseudomonas aeruginosa* | <0.01 | <0.01 | <0.01 | <0.01 | <0.01 | <0.01 |
| *Escherichia coli* | <0.01 | <0.01 | <0.01 | <0.01 | 21 | <0.01 |
| *Serratia marcescens* | <0.01 | <0.01 | <0.01 | <0.01 | 20 | <0.01 |
| *Candida albicans* | <0.01 | <0.01 | <0.01 | <0.01 | 20 | 11 |
| *Aspergillus niger* | <0.01 | <0.01 | <0.01 | <0.01 | 36 | 0.53 |

Test Example 2
Anti-microbial Effect of GLOKILL PQ

Test solutions as formulated in Table 4 (g/100 ml) were prepared as disinfectants for contact lens care containing compound (3) as an anti-microbial agent. Control solutions used in this test were a solution of ReNu (Bausch & Lomb) containing 0.0001% of a polymer compound of biguanide, i.e., polyhexamethylene biguanide, and a solution of Opti-Free (Alcon Laboratories Inc.) containing 0.001% of a polymer compound of quaternary ammonium salt, i.e., polyquad.

Anti-microbial efficacy test was conducted for the test solutions and the control solutions according to the USP preservative effectiveness test by using *Staphylococcus aureus, Pseudomonas aeruginosa, Serratiamarcescens, Candida albicans,* and *Aspergillus niger.* The viable count of the microorganisms was determined 4 hours after the initiation of the test to evaluate the anti-microbial effect. It is clear that the formulations comprising the anti-microbial agent of the present invention have a sufficient anti-microbial efficacy at a very low concentration and in particular the formulations have greater fungicidal efficacy than those of the commercially available disinfectants for contact lens care. In addition, it has been revealed that the test solution formulated with potassium aspartate as an isotonizing agent also has a high anti-microbial efficacy.

TABLE 4

|  | Formulations | | | |
| --- | --- | --- | --- | --- |
|  | 1 | 2 | 3 | 4 |
| Compound (3) | 0.0020 | 0.0010 | 0.0002 | 0.0020 |
| Potassium aspartate | — | — | — | 2.0000 |
| Boric acid | 1.0000 | 1.0000 | 1.0000 | 1.0000 |

TABLE 4-continued

| | Formulations | | | |
|---|---|---|---|---|
| | 1 | 2 | 3 | 4 |
| Borax | 0.2000 | 0.2000 | 0.2000 | 0.2000 |
| Poloxamer 407 | 0.1000 | 0.1000 | 0.1000 | 0.1000 |
| Sodium hydroxide | Adequate amount | Adequate amount | Adequate amount | Adequate amount |
| Sterile purified water | Adequate amount | Adequate amount | Adequate amount | Adequate amount |
| pH | 7.4 | 7.4 | 7.4 | 7.4 |

TABLE 5

Reduction ratio of viable count*

| | Formulations | | | | | |
|---|---|---|---|---|---|---|
| Strains | 1 | 2 | 3 | 4 | ReNu | Opti-Free |
| Staphylococcus epidermis | −5.9 | −5.9 | −4.5 | −5.9 | −3.7 to 5.5 | −5.5 to 6.3 |
| Pseudomonas aeruginosa | −5.0 to −6.2 | −4.3 to −4.4 | −3.9 to −4.2 | −5.0 to −6.2 | −3.9 to −5.7 | −5.7 |
| Serratia marcescens | −4.0 | −4.0 | −3.2 | −4.0 | −3.8 to −6.2 | −2.3 to −4.0 |
| Candida albicans | −4.6 to −5.6 | −3.7 | −1.4 | −4.6 to −5.6 | −1.9 | 0 |
| Aspergillus niger | −1.4 | −1.4 | −1.3 | −1.4 | 0 | 0 |

*The reduction ratio of viable count is indicated as Log 10 of viable count at hour hours after the initiation of the test/viable count at the initiation of the test Test Example 3

Cytotoxicity of the compound (3) was evaluated by conducting a test according to the method of Neutral red assay using rabbit corneal epithelial cells of a CornePack kit (Kurabo Industries, Ltd.).

The frozen cells of the primary culture were inoculated at a density of 4000 cells/cm$^2$ in a 25-cm$^2$ flask. The cells were cultured at 37° C. under an atmosphere of 5% $CO_2$ for 5 days (the secondary culture) and then 100 μl aliquots of them were inoculated in the wells of a 96-well multi-plate at a cell density of 2500 cells/well. The culture was continued at 37° C. under an atmosphere of 5% $CO_2$ for 3 days (tertiary culture). Respective compounds to be tested were diluted with the culture medium to the concentrations as indicated in Table 6, to prepare the test solutions. A 100 μl aliquot of the solutions was added into each well containing the corneal epithelial cells of the tertiary culture. The cells were further cultured at 37° C. under an atmosphere of 5% $CO_2$ for 2 days. A 100 μl aliquot of a Neutral red solution (about 150 μg/ml) was added into each well. The cells were further cultured at 37° C. under an atmosphere of 5% $CO_2$ for 2 hours to incorporate Neutral red into lysosomes of the viable cells. Then the culture supernatants were discarded by inverting the plate. A 200 μl aliquot of a solution containing formalin and calcium chloride were added into each well and the cells were fixed for 1 minute to improve the cell adhesion to the plate. The remaining Neutral red was washed out from the wells. Subsequently, the supernatants in the wells were discarded and 100 μl aliquots of a mixture consisting of acetic acid and ethanol were added to the wells. The plate was allowed to stand for 20 minutes to extract Neutral red incorporated in the viable cells. The amount of Neutral red was determined by measuring the absorbance at a wavelength of 540 nm. The averaged absorbance value of the blank (the measured value, which was obtained by the same assay procedure but in the absence of Neutral red, for the untreated control cells cultured under the same condition) was subtracted from the measured value of the sample to give the correction absorbance value. The viable cell rate was calculated from the ratio of the sample absorbance to the absorbance for the untreated cells according to the following equation. The result is shown in Table 6.

Viable cell rate in each plate=(Averaged absorbance of each test solution/Averaged absorbance of the untreated control)×100

TABLE 6

| Concentration of test solution (μg/ml) | Compound (3) | Chlorhexidine gluconate | Benzalkonium chloride |
|---|---|---|---|
| 0.5 | 84% | — | 60% |
| 1.0 | 91% | 103% | 52% |
| 2.5 | 93% | 74% | 49% |
| 5.0 | 105% | 49% | 2% |
| 10.0 | 47% | 3% | — |
| 20.0 | 6% | — | — |

This result clearly shows that the above-described compound (3) is highly safe, since it exhibits only negligible toxicity to corneal epithelial cells, as compared to chlorhexidine gluconate and benzalkonium chloride.

Test Example 4

The above-described compound (3) was tested for the adsorption onto soft contact lens.

Specifically, a soft contact lens, SUREVUE (Johnson & Johnson) was immersed for 72 hours in each test solution of the formulations (g/100 ml) shown in Table 7. The test solution was changed twice a day. Then the lens was taken out from the solution and the solution remaining on the lens was removed with a piece of filter paper. Subsequently, the lens was placed on a Mueller-Hinton agar plate containing inoculated Staphylococcus aureus ATCC6538 ($10^6$ cells/ml). The culture was continued at 30° C. for 24 hours. The size of the resulting growth inhibition ring was measured to evaluate the degree of adsorption and release of the antimicrobial agent. The result is shown in Table 8.

TABLE 7

| | Formulations | | | | | |
|---|---|---|---|---|---|---|
| | 0 | 1 | 2 | 3 | 4 | 5 |
| Compound (3) | 0.0010 | 0.0010 | 0.0005 | 0.0001 | | |
| Polyhexamethylene biguanide | | | | | 0.0005 | 0.0001 |
| Sodium chloride | | 0.5000 | 0.5000 | 0.5000 | 0.5000 | 0.5000 |
| Boric acid | | 0.5000 | 0.5000 | 0.5000 | 0.5000 | 0.5000 |
| Borax | | 0.1000 | 0.1000 | 0.1000 | 0.1000 | 0.1000 |
| Poloxamer 407 | | 0.1000 | 0.1000 | 0.1000 | 0.1000 | 0.1000 |
| Sodium edetate | | 0.0500 | 0.0500 | 0.0500 | 0.0500 | 0.0500 |
| Sodium hydroxide | Adequate amount | Adequate amount | Adequate amount | Adequate amount | Adequate amount | Adequate amount |
| Sterile purified water | Adequate amount | Adequate amount | Adequate amount | Adequate amount | Adequate amount | Adequate amount |
| pH | 7.4 | 7.4 | 7.4 | 7.4 | 7.4 | 7.4 |

TABLE 8

| | Formulations | | | | | |
|---|---|---|---|---|---|---|
| | 0 | 1 | 2 | 3 | 4 | 5 |
| Width of inhibition zone (mm) | 0 | 0 | 0 | 0 | 2 | 0 |

Width of inhibition zone = (Diameter of inhibition ring − Diameter of lens) ÷ 2

The results clearly shows that the above-described compound (3) is not absorbed onto soft contact lenses within the concentration range in which it is effective as an antimicrobial agent.

Test Example 5

An ophthalmic mucous membrane irritation test was conducted for the above-described compound (3). Healthy males of mature white rabbits were used in the present test. The irritability was evaluated by giving the test solution into one eye of each rabbit and physiological saline in the other eye in the form of eye-drops: a 100 μl aliquot of each solution was dropped in an eye by using a micropipette. Specifically, the administration was carried out as follows: each solution was dropped into the conjunctival sac while gently pulling the lower eyelid; the pulled eyelid was held for 30 seconds to prevent the solution from overflowing. Both eyes of each rabbit were observed for the symptoms caused by the irritants by using a slit lamp immediately after dropping the solutions as well as 3, 6, 24, 48, and 72 hours after dropping. The scoring was carried out according to the criteria of the Draize method. As shown in Table 9, it can be concluded that none of the test solutions are irritating at all.

TABLE 9

| Animal No. | Soln. for right eye Soln. for left eye | Before dropping | Just after dropping | 3 hrs | 6 hrs | 24 hrs | 48 hrs | 72 hrs | Test results |
|---|---|---|---|---|---|---|---|---|---|
| 1 | Soln. X | 0 | 0 | 0 | 0 | 0 | 0 | 0 | Not |
|   | Saline  | 0 | 0 | 0 | 0 | 0 | 0 | 0 | irritant |
| 2 | Soln. X | 0 | 0 | 0 | 0 | 0 | 0 | 0 | Not |
|   | Saline  | 0 | 0 | 0 | 0 | 0 | 0 | 0 | irritant |
| 3 | Soln. X | 0 | 0 | 0 | 0 | 0 | 0 | 0 | Not |
|   | Saline  | 0 | 0 | 0 | 0 | 0 | 0 | 0 | irritant |
| 4 | Soln. Y | 0 | 0 | 0 | 0 | 0 | 0 | 0 | Not |
|   | Saline  | 0 | 0 | 0 | 0 | 0 | 0 | 0 | irritant |
| 5 | Soln. Y | 0 | 0 | 0 | 0 | 0 | 0 | 0 | Not |
|   | Saline  | 0 | 0 | 0 | 0 | 0 | 0 | 0 | irritant |
| 6 | Soln. Y | 0 | 0 | 0 | 0 | 0 | 0 | 0 | Not |
|   | Saline  | 0 | 0 | 0 | 0 | 0 | 0 | 0 | irritant |
| 7 | Soln. Z | 0 | 0 | 0 | 0 | 0 | 0 | 0 | Not |
|   | Saline  | 0 | 0 | 0 | 0 | 0 | 0 | 0 | irritant |
| 8 | Soln. Z | 0 | 0 | 0 | 0 | 0 | 0 | 0 | Not |
|   | Saline  | 0 | 0 | 0 | 0 | 0 | 0 | 0 | irritant |
| 8 | Soln. Z | 0 | 0 | 0 | 0 | 0 | 0 | 0 | Not |
|   | Saline  | 0 | 0 | 0 | 0 | 0 | 0 | 0 | irritant |

Soln. X: 0.001% compound (3)
Soln. Y: 0.01% compound (3)
Soln. Z: 1.0% compound (3)

INDUSTRIAL APPLICABILITY

The ophthalmic solutions of the present invention can be provided in the form of stable aqueous liquid solutions and can be used for a long period of time at normal temperatures. Furthermore, the solutions are applicable for all types of materials utilized for hard contact lenses, gas-permeable hard contact lenses, and soft contact lenses. The solutions also have practically no influence on the physical properties of the lenses and do not irritate the eye.

What is claimed is:

1. An ophthalmic solution comprising a polymer comprising a main chain, quaternary ammonium salts, alkylene groups, and hydroxyl groups on a repetitive unit of the main chain.

2. The ophthalmic solution of claim 1, wherein the polymer comprises a repetitive unit represented by the following formula:

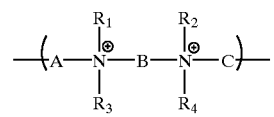

wherein each of $R_1$, $R_2$, $R_3$, and $R_4$ group having 1 to 3 carbon atoms; and each of A, B, and C independently represents an alkylene group having 1 to 3 carbon atoms, an oxyalkylene group having 1 to 3 carbon atoms, or an alkylene group having 1 to 4 carbon atoms and one or more hydroxyl groups; and counter ion(s); provided that at least one of A, B, and C contains one or more hydroxyl groups.

3. The ophthalmic solution of claim 2, wherein the repetitive unit is represented by the following formula:

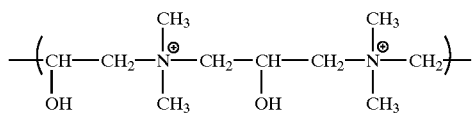

or the following formula:

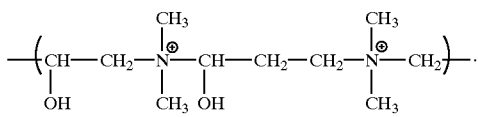

4. The ophthalmic solution of claim 2, wherein the counter ion is chloride ion(s).

5. The ophthalmic solution of claim 1, wherein the concentration of the polymer in the ophthalmic solution ranges from 0.00001 to 1.0 w/v %.

6. The ophthalmic solution of claim 5, formulated for use as a disinfectant for ophthalmic apparatuses.

7. The ophthalmic solution of claim 1, wherein the concentration of the polymer in the ophthalmic solution ranges from 0.00001 to 0.01 w/v %.

8. The ophthalmic solution of claim 7, formulated for use as an eye drop, an eyewash solution, or a contact lens care solution selected from the group consisting of a cleaning solution, a storing solution, a disinfectant, a cleaning-storing solution, and a cleaning disinfecting-storing solution.

9. The ophthalmic solution of claim 8, wherein the polymer has a molecular weight adequate to ensure that it is not substantially adsorbed onto and/or absorbed into hydrophilic contact lenses.

10. The ophthalmic solution of claim 9, wherein the polymer has a molecular weight ranging from 1000 to 100,000.

11. The ophthalmic solution of claim 1, further comprising aspartic acid and/or a salt thereof.

12. The ophthalmic solution of claim 11, wherein the salt is selected from the group consisting of sodium aspartate, potassium aspartate, and magnesium aspartate.

13. An ophthalmic solution comprising an opthalmically acceptable additive and a polymer comprising a main chain, quaternary ammonium salts, alkylene groups and hydroxyl groups on a repetitive unit of the main chain.

14. The ophthalmic solution of claim 1, wherein the concentration of the polymer in the ophthalmic solution ranges from 0.00005 to 0.005 w/v %.

15. The ophthalmic solution of claim 1, wherein the concentration of the polymer in the ophthalmic solution ranges from 0.00001 to 0.001 w/v %.

16. The ophthalmic solution of claim 5, further comprising aspartic acid and/or a salt thereof.

17. The ophthalmic solution of claim 5, further comprising sodium aspartate, potassium aspartate, or magnesium aspartate.

18. The ophthalmic solution of claim 13, wherein the additive is selected from the group consisting of viscoelastic agents, chelating agents, and nonionic surfactants.

19. The ophthalmic solution of claim 13, wherein the additive is selected from the group consisting of dipotassium glycyrrhizinate, sodium edetate, hydroxyethyl cellulose, hydroxypropylmethyl cellulose, polyvinylpyrrolidone, and poloxamer.

20. The ophthalmic solution of claim 11, further comprising an ophthalmically acceptable additive selected from the group consisting of viscoelastic agents, chelating agents, and nonionic surfactants.

21. The ophthalmic solution of claim 11, further comprising an ophthalmically acceptable additive selected from the group consisting of dipotassium glycyrrhizinate, sodium edetate, hydroxyethyl cellulose, hydroxypropylmethyl cellulose, polyvinylpyrrolidone, and poloxamer.

22. The ophthalmic solution of claim 16, further comprising an ophthalmically acceptable additive selected from the group consisting of viscoelastic agents, chelating agents, and nonionic surfactants.

23. The ophthalmic solution of claim 16, further comprising an ophthalmically acceptable additive selected from the group consisting of dipotassium glycyrrhizinate, sodium edetate, hydroxyethyl cellulose, hydroxypropylmethyl cellulose, polyvinylpyrrolidone, and poloxamer.

* * * * *

UNITED STATES PATENT AND TRADEMARK OFFICE
CERTIFICATE OF CORRECTION

PATENT NO.    : 6,528,048 B1
DATED         : March 4, 2003
INVENTOR(S)   : Tetsuo Koike and Michiko Tsujimoto It is certified that error appears in the above-identified patent and that said Letters Patent is hereby corrected as shown below:

<u>Title page,</u>
Item [54], Title, replace "[+54]" with -- [54] --.

<u>Column 16,</u>
Line 23, after "$R_4$" insert -- independently represents an alkyl --.

Signed and Sealed this

Eleventh Day of May, 2004

JON W. DUDAS
*Acting Director of the United States Patent and Trademark Office*